US012428358B2

(12) United States Patent
Wu et al.

(10) Patent No.: US 12,428,358 B2
(45) Date of Patent: Sep. 30, 2025

(54) METHOD FOR PREPARING A COAL-BASED LINEAR ALKYLBENZENE

(71) Applicant: Inner Mongolia Yitai Coal-based New Materials Research Institute Co., Ltd., Inner Mongolia (CN)

(72) Inventors: Jingwei Wu, Inner Mongolia (CN); Yue Zhang, Inner Mongolia (CN); Zhen Qian, Inner Mongolia (CN); Zhifei Li, Inner Mongolia (CN); Xiaolong Zhang, Inner Mongolia (CN); Xinping Zhang, Inner Mongolia (CN); Xiangqiang Shi, Inner Mongolia (CN); Zhengxu Ao, Inner Mongolia (CN); Xuanheng Guo, Inner Mongolia (CN); Juncheng Li, Inner Mongolia (CN); Haiguo Wang, Inner Mongolia (CN); Changyu Ren, Inner Mongolia (CN)

(73) Assignee: Inner Mongolia Yitai Coal-based New Materials Research Institute Co., Ltd., Inner Mongolia (CN)

( * ) Notice: Subject to any disclaimer, the term of this patent is extended or adjusted under 35 U.S.C. 154(b) by 0 days.

(21) Appl. No.: 18/556,713

(22) PCT Filed: Nov. 25, 2022

(86) PCT No.: PCT/CN2022/134297
§ 371 (c)(1),
(2) Date: Oct. 23, 2023

(87) PCT Pub. No.: WO2024/021397
PCT Pub. Date: Feb. 1, 2024

(65) Prior Publication Data
US 2025/0084015 A1    Mar. 13, 2025

(30) Foreign Application Priority Data

Jul. 27, 2022  (CN) .......................... 202210890163.6

(51) Int. Cl.
*C07C 2/66*  (2006.01)

(52) U.S. Cl.
CPC ............ *C07C 2/66* (2013.01); *C07C 2529/06* (2013.01)

(58) Field of Classification Search
CPC ... C07C 2/66; C07C 2529/06; C07C 2529/70; C07C 2531/10; B01J 37/0081;
(Continued)

(56) References Cited

U.S. PATENT DOCUMENTS

| 8,314,045 B1 | 11/2012 | Sinoncelli et al. |
| 2005/0187417 A1* | 8/2005 | Briot ........................ C07C 2/66 585/467 |

(Continued)

FOREIGN PATENT DOCUMENTS

| CN | 1064475 A | 9/1992 |
| CN | 101961660 A | 2/2011 |

(Continued)

OTHER PUBLICATIONS

International Search Report and Written Opinion for PCT/CN2022/134297 mailed Apr. 23, 2023, 9 pages (no translation).

(Continued)

*Primary Examiner* — Ali Z Fadhel
(74) *Attorney, Agent, or Firm* — Myers Bigel, P.A.

(57) ABSTRACT

The present disclosure provides a method for preparing a coal-based linear alkylbenzene, wherein the coal-based linear alkylbenzene is prepared by an alkylation reaction using a coal-based Fischer-Tropsch synthetic oil and a benzene as reaction raw materials and using a molecular sieve loaded with a strong acid cation exchange resin as a catalyst; the strong acid cation exchange resin has an acid strength $\geq 0.9$ mmol/g [$H^+$]; and the coal-based Fischer-Tropsch synthetic oil comprises a linear olefin with a carbon number range of (Continued)

C9-C13. In the present disclosure, the strong acid cation exchange resin is loaded into pores and onto a surface of the molecular sieve, which has better effect on the selectivity to the alkylbenzene product. The product has a high straight chain ratio, has a high selectivity for 2-position substitution, and may maintain a relatively high olefin conversion rate, thereby significantly increasing the lifetime of the catalyst.

10 Claims, 1 Drawing Sheet

(58) Field of Classification Search
CPC .............. B01J 2229/40; B01J 2229/42; B01J 29/7007; C10G 229/205; C10G 2300/1022
See application file for complete search history.

(56) References Cited

U.S. PATENT DOCUMENTS

| | | | |
|---|---|---|---|
| 2007/0142481 A1* | 6/2007 | Steynberg | C10G 2/344 518/726 |
| 2009/0000185 A1* | 1/2009 | Aulich | C10L 1/04 44/308 |

FOREIGN PATENT DOCUMENTS

| | | |
|---|---|---|
| CN | 106281444 A | 1/2017 |
| CN | 108341735 A | 7/2018 |
| CN | 115043693 A | 9/2022 |
| WO | 2004080929 A2 | 9/2004 |

OTHER PUBLICATIONS

Jian Liu, et al., "Research progress in long chain catalytic alkylation of aromatic hydrocarbons", Chemical Industry and Engineering Progress, 2020, 39(5): 1744-1755. translated abstract.

Wang, Hai, et al., "Nafion/SiO2 Nanocomposites: High Potential Catalysts for Alkylation of Benzene with Linear C9-C13 Alkenes", Chinese Chemical Letters vol. 13, No. 11, pp. 1121-1124, 2002 http://www.imm.ac.cn/journal/ccl.html.

Extended European Search Report corresponding to European Application No. 22940944.6 (8 pages) (Feb. 18, 2025).

De Klerk, Arno, "Fischer-Tropsch Process", Kirk-Othmer Encyclopedia of Chemical Technology (Jan. 18, 2013).

First Chinese Office Action corresponding to CN Application No. 202210890163.6; issued Mar. 14, 2023 (14 pages, including English translation).

Second Chinese Office Action corresponding to CN Application No. 202210890163.6; issued Oct. 14, 2023 (13 pages, including English translation).

Luo, Jiazhong, et al., "Nafion Resin as a Superacid Catalyst in Organic Synthesis", Ion Exchange and Adsorption 8(3):267-279, 1992, translated abstract.

Luo, Fang-Tao, et al., "Review on high value processing and utilization route of low temperature Fischer-Tropsch synthesis products and coal-to-liquids industrial development direction", Petrochemical Technology & Application 39(4):293-297, 2021, translated abstract.

* cited by examiner

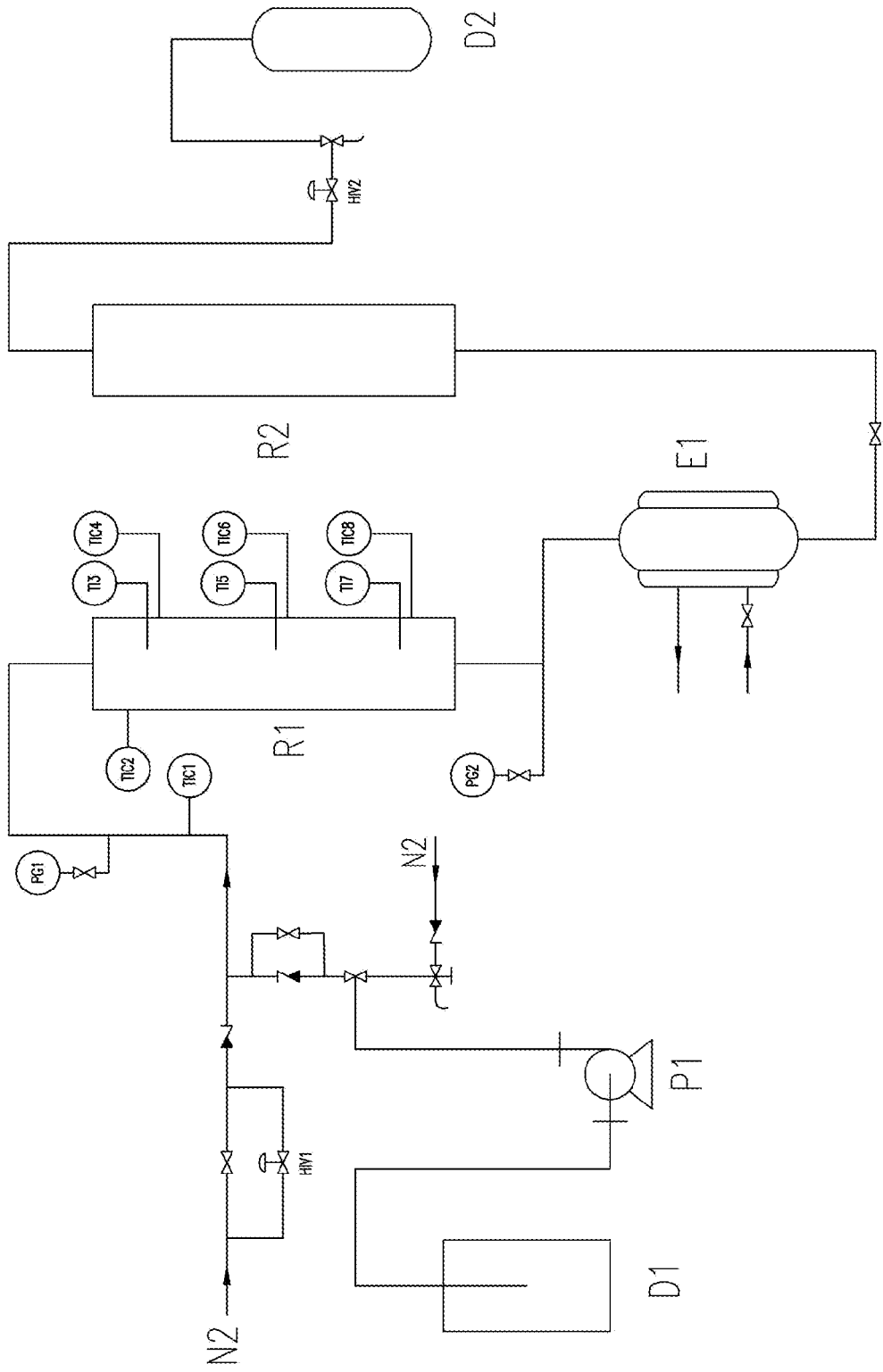

METHOD FOR PREPARING A COAL-BASED LINEAR ALKYLBENZENE

CROSS REFERENCE TO RELATED APPLICATION

The present application is a 35 U.S.C. 371 national stage application of PCT International Application No. PCT/CN2022/134297 filed on Nov. 25, 2022, which claims a priority of Chinese Patent Application No. 202210890163.6, filed on Jul. 27, 2022 with a title of "Method for preparing a coal-based linear alkylbenzene", each of which is incorporated herein by reference in their entireties.

TECHNICAL FIELD

The present disclosure relates to the technical field of coal chemical industry, and particularly to a method for preparing a coal-based linear alkylbenzene.

BACKGROUND

Alkylbenzenes are important intermediates for chemical industry production. Alkylbenzenes are mainly synthesized through the alkylation reaction between benzene and olefins. Currently, main alkylation catalysts comprise heteropolyacid catalysts, molecular sieve catalysts, ionic liquid catalysts, and so on.

The catalysts for alkylation reaction specifically comprise the following aspects:

(1) Heteropolyacid Catalysts

Heteropolyacid catalysts are a class of protonic acid catalysts with complex structures, which are mainly formed by atoms such as P, Si, Fe and Co coordinated and bridged with oxygen atoms in a specific structure.

The application of heteropolyacid acidic catalysts in the synthesis of alkylbenzenes has advantages of being green and pollution-free and less corrosive to alkylbenzene production equipment, but has problems such as low catalyst activity and relatively high reaction requirements that should be paid attention to.

(2) Molecular Sieve Catalysts

Molecular sieve catalysts are a class of aluminosilicate catalysts with structures of $SiO_4$ tetrahedron and $AlO_4$ tetrahedron. They have advantages of high acidity, and being reproducible, easy to separate, environment friendly and so on, and are widely used in the synthesis reaction of alkylbenzenes.

The application of molecular sieve catalysts in the production of alkylbenzenes has disadvantages. For example, more by-products and impurities are formed, catalyst is rapidly deactivated, and production cost is high, which limit the application of molecular sieve catalysts in the industry.

(3) Ionic Liquid Catalysts

Ionic liquid catalysts are a class of salts which are liquids at low temperature, and mainly composed of organic nitrogen-containing heterocyclic cations and inorganic complex anions. They have advantages of super high acidity, a wide liquid temperature range, a low vapor pressure, a reusability and a less environmental pollution, and attracted much attention of researchers. Existing methods for removing oxygenated compounds through a molecular sieve catalytic reaction suffer from problems of low reaction temperature, short catalyst lifetime and low selectivity to olefins.

Ionic liquid in the synthesis of alkylbenzenes can be evenly distributed in the liquid phase, and the product is easy to separate, but the catalytic activity will be affected by the $H^+$ concentration in the ionic liquid, which is detrimental to the application of ionic liquid catalysts in the alkylbenzene synthesis industry.

A Fischer-Tropsch oil (i.e., a coal-based synthetic oil) contains about 10000 ppm oxygenated compounds and about 500 ppm water, and benzene as a raw material also contains about 500 ppm water. Complexation or substitution reactions between oxygenated compounds such as an alcohol, an aldehyde, and a ketone and the molecular sieve catalyst will occur. Oxygenated compounds will make a portion of the catalyst be poisoned and deactivated. Also, water will compete for active sites in the catalyst, significantly reducing the lifetime of the catalyst. Therefore, the preparation of alkylbenzenes using a coal-based synthetic oil as a reaction raw material still needs to be further investigated by researchers.

SUMMARY

An object of the present disclosure is to provide a method for preparing a coal-based linear alkylbenzene. The method of the present disclosure can maintain relatively high olefin conversion rate without a treatment of removing water or oxygenates from the reaction raw materials, significantly increasing the lifetime of the catalyst.

The present disclosure provides a method for preparing a coal-based linear alkylbenzene, wherein the coal-based linear alkylbenzene is prepared by an alkylation reaction using a coal-based Fischer-Tropsch synthetic oil and a benzene as reaction raw materials and using a molecular sieve loaded with a strong acid cation exchange resin as a catalyst;

the strong acid cation exchange resin has an acid strength ≥0.9 mmol/g [$H^+$]; and the coal-based Fischer-Tropsch synthetic oil comprises a linear olefin with a carbon number range of C9-C13, and the linear olefin with a carbon number range of C9-C13 accounts for 30-35% by weight of the coal-based Fischer-Tropsch synthetic oil.

Preferably, a molar ratio of the benzene to the coal-based Fischer-Tropsch synthetic oil (on the basis of the linear olefin with a carbon number range of C9-C13) is in a range of (20-1): 1. That is, a benzene-to-olefin ratio is in a range of 20:1-1:1.

Preferably, the reaction raw materials are not subjected to a treatment of removing water or oxygenates therein.

Preferably, the molecular sieve is one or more selected from the group consisting of a Hβ molecular sieve, a HY molecular sieve and a MCM molecular sieve.

Preferably, the molecular sieve has a porous structure in which pores with a pore size of 1-10 nm account for 10-20%, and pores with a pore size of 100-200 nm accounts for 90-80%.

Preferably, a mass ratio of the strong acid cation exchange resin to the molecular sieve is in a range of 1:9-4:6.

Preferably, the alkylation reaction is carried out at a temperature in a range of 70-200° C., a pressure in a range of 1-4 MPa and a space velocity in a range of 0.5-10 $h^{-1}$.

Preferably, the coal-based Fischer-Tropsch synthetic oil has an oxygenated compound content in a range of 1-12000 ppm, such as 9000-12000 ppm; and a water content in a range of 1-550 ppm, such as 400-550 ppm.

Preferably, the benzene has a water content in a range of 1-550 ppm.

Preferably, the strong acid cation exchange resin is loaded into pores of the molecular sieve.

BRIEF DESCRIPTION OF DRAWINGS

To more clearly illustrate the technical solutions in the embodiments of the present disclosure or in prior art, the drawings to be used in the specification of the embodiments or prior art will be briefly described below. Obviously, the drawings described are only embodiments of the present disclosure, and for those skilled in the art, other drawings can be obtained according to the provided drawings without inventive efforts.

FIG. 1 is a process flow diagram using a fixed bed reactor in the present disclosure;

wherein PG1 represents a local pressure gauge at the reactor inlet, PG2 represents a local pressure gauge at the reactor outlet, HIV1 represents a gas phase flow control valve for raw materials, HIV2 represents a system pressure control valve, TIC1 represents a reactor inlet pipe temperature controller, TI2 represents a reactor bed temperature indicator, TI3 represents a reactor upper segment temperature indicator, TIC4 represents a reactor upper segment temperature controller, TI5 represents a reactor middle segment temperature indicator, TIC6 represents a reactor middle segment temperature controller, TI7 represents a reactor lower segment temperature indicator, TIC8 represents a reactor lower segment temperature controller, D1 represents a raw material tank, D2 represents a product collection tank, R1 represents a reactor, E1 represents a water cooler for a product, P1 represents a raw material metering pump.

DETAILED DESCRIPTION

The Fischer-Tropsch synthetic oil in the present application is obtained by a Fischer-Tropsch process. The Fischer-Tropsch process, also known as F-T synthesis, is a process to synthesize a liquid hydrocarbon by using syngas (a gas mixture of carbon monoxide and hydrogen) as a raw material under a catalyst and an appropriate condition. It was developed in 1925 by German chemists, Franz Fischer and Hans Tropsch, who worked at the Max Planck Institute for Coal Research in Muelheim on the Ruhr. The Fischer-Tropsch synthetic oil has a carbon number in a range from 4 to 20. However, in the present disclosure, only the linear olefin with a carbon number range of C9-C13 contained therein are used. In the Fischer-Tropsch synthetic oil, the linear olefin with a carbon number range of C9-C13 accounts for about 30-35% by weight.

The present disclosure provides a method for preparing a coal-based linear alkylbenzene, wherein the coal-based linear alkylbenzene is prepared by an alkylation reaction using a coal-based Fischer-Tropsch synthetic oil and a benzene as reaction raw materials and using a molecular sieve loaded with a strong acid cation exchange resin as a catalyst;

the strong acid cation exchange resin has an acid strength ≥0.9 mmol/g [$H^+$]; and the coal-based Fischer-Tropsch synthetic oil comprises a linear olefin with a carbon number range of C9-C13, and the linear olefin with a carbon number range of C9-C13 accounts for 30-35% by weight of the coal-based Fischer-Tropsch synthetic oil.

In the present disclosure, the equipment is firstly purged with an air pump, the liquid transfer pump is calibrated, and then the catalyst is charged. In the present disclosure, quartz sand and quartz wool are added into the lower portion of the reactor, then the catalyst is mixed with quartz sand or inert ceramic balls in a certain proportion and charged into the constant temperature zone, and quartz wool is filled into the upper portion.

In the present disclosure, the catalyst is a molecular sieve loaded with a strong acid cation exchange resin which has an acid strength ≥0.9 mmol/g [$H^+$]; the molecular sieve is one or more selected from the group consisting of a Hβ molecular sieve, a HY molecular sieve and a MCM molecular sieve; and the molecular sieve has a pore structure in which pores with a pore size of 1-10 nm account for 10-20%, and pores with a pore size of 100-200 nm accounts for 90-80%. The strong acid cation exchange resin is loaded into the pores and onto a surface of the molecular sieve, such that the catalyst of the present application has better effect on the selectivity (the product having a higher straight chain ratio and a higher selectivity for 2-position substitution) and high acidity. A mass ratio of the strong acid cation exchange resin to the molecular sieve is preferably in a range of 1:9-4:6, such as 1:9, 2:8, 3:7 or 4:6, and preferably in a range with any of the above numbers as the upper limit or lower limit.

In the present disclosure, after loading the catalyst, the pipeline of the equipment is purged with nitrogen, then the water content and the oxygenated compound content in the coal-based Fischer-Tropsch synthetic oil are detected, the water content in the benzene is detected, and the coal-based Fischer-Tropsch synthetic oil and the benzene are mixed in a predetermined benzene-to-olefin ratio in a range of 1-20:1 to obtain the benzene-olefin raw material.

In the present disclosure, the Fischer-Tropsch oil (i.e., a coal-based synthetic oil) as a raw material contains about 10000 ppm oxygenated compounds and about 500 ppm water, and the benzene as a raw material also contains about 500 ppm water. In the coal-based Fischer-Tropsch synthetic oil, in terms of the linear olefin with a carbon number range of C9-C13 which is preponderant, the benzene-to-olefin ratio (i.e., a molar ratio of the benzene to the linear olefin of C9-C13) is preferably in a range of (20-1): 1, more preferably in a range of (15-5): 1, such as 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, and 1:1, and preferably in a range with any of the above numbers as the upper limit or lower limit.

Then, in the present disclosure, the equipment is rinsed by introducing benzene into the bed and is purged with nitrogen, with the rinsing repeated three times. Then, the temperature of the reactor is adjusted to the reaction temperature, and the reactor is pressurized to the reaction pressure by introducing benzene.

In the present disclosure, the temperature for the alkylation reaction is preferably in a range of 70-200° C., more preferably in a range of 90-150° C., such as 70° C., 80° C., 90° C., 100° C., 110° C., 120° C., 130° C., 140° C., 150° C., 160° C., 170° C., 180° C., 190° C., and 200° C., and preferably in a range with any of the above numbers as the upper limit or lower limit; and the pressure for the alkylation reaction is preferably in a range of 1-4 MPa, and more preferably in a range of 2-3 MPa.

After the pressure is constant, the raw material is switched to the benzene-olefin raw material, and the benzene-olefin raw material is passed through the catalyst bed to perform the alkylation reaction, wherein the benzene-olefin raw material preferably has a space velocity in a range of 0.5-10 $h^{-1}$, more preferably in a range of 1-8 $h^{-1}$, such as 0.5 $h^{-1}$, 1 $h^{-1}$, 2 $h^{-1}$, 3 $h^{-1}$, 4 $h^{-1}$, 5 $h^{-1}$, 6 $h^{-1}$, 7 $h^{-1}$, 8 $h^{-1}$, 9 $h^{-1}$, and 10 $h^{-1}$, and preferably in a range with any of the above numbers as the upper limit or lower limit.

Sampling begins after the system is filled with liquid. The olefin conversion rate is calculated through a chromatographic analysis, and the final product is collected.

The present disclosure provides a method for preparing a coal-based linear alkylbenzene, wherein the coal-based linear alkylbenzene is prepared by an alkylation reaction using a coal-based Fischer-Tropsch synthetic oil and a benzene as reaction raw materials and using a molecular sieve loaded with a strong acid cation exchange resin as a catalyst; the strong acid cation exchange resin has an acid strength ≥0.9 mmol/g [H+] and such an acid strength is selected because the inventors have found that the conversion rate for the reaction will less than 60% if the acid strength is less than such a value; and the coal-based Fischer-Tropsch synthetic oil comprises a linear olefin with a carbon number range of C9-C13. Higher the catalytic activity of the catalyst in the present disclosure, the need for the reaction requirements is lower; the by-products and impurities are less, the lifetime of the catalyst is longer, and the effect of the water and oxygenated compounds in the raw materials on the lifetime and activity of the catalyst is less, and the production cost is lower; also, the catalytic activity will not be affected by the $H^+$ concentration.

Therefore, the present disclosure provides a method for preparing a coal-based linear alkylbenzene, wherein the coal-based linear alkylbenzene is prepared by an alkylation reaction using a coal-based Fischer-Tropsch synthetic oil and a benzene as reaction raw materials and using a molecular sieve loaded with a strong acid cation exchange resin as a catalyst; the strong acid cation exchange resin has an acid strength ≥0.9 mmol/g [H+]; and the coal-based Fischer-Tropsch synthetic oil is calculated in terms of a linear olefin with a carbon number range of C9-C13. In the present disclosure, the strong acid cation exchange resin is loaded into pores and onto a surface of the molecular sieve, which has better effect on selectivity of the alkylbenzene product. The product has a high straight chain ratio (97% or more), has a high selectivity for 2-position substitution, and may maintain a relatively high olefin conversion rate (60% or more) without a treatment of removing water or oxygenates from the reaction raw materials, thereby significantly increasing the lifetime of the catalyst.

In order to further illustrate the present disclosure, the method for preparing a coal-based linear alkylbenzene provided in the present disclosure will be described in detail below with reference to examples. However, the examples cannot be construed as limiting the protection scope of the present disclosure.

In all the following examples, a resin with sulfonating agent (acetosulfonate):polystyrene=2:1 (molar ratio) was used.

Example 1

Experimental instruments and chemicals: a high purity nitrogen, a quartz wool, a quartz sand or an inert ceramic balls, a fixed bend reactor, a piston pump, a C9-C13 Fischer-Tropsch oil, a benzene (99.9%), a YT-02 resin catalyst, and a gas chromatograph.

The YT-02 resin catalyst may be prepared as follows: the resin with sulfonating agent (acetosulfonate):polystyrene=2:1 (molar ratio) and a Hβ molecular sieve were loaded in a mass ratio of 2:7. The loading process comprised melting the resin to a liquid state, soaking the molecular sieve into the resin, then thoroughly mixing, for example, for 12 h, and then baking it to dryness, for example, baking at 105° C. for 8 h. The resulting YT-02 resin catalyst had an acid strength of 1 mmol/g [H+].

Preparation for the Experiment:
① The equipment was purged with an air pump; and the liquid transfer pump was calibrated.
② The catalyst was charged.

Quartz sand and quartz wool were added into the lower portion of the reactor, then the catalyst was mixed with quartz sand in a certain proportion and charged into the constant temperature zone, and quartz wool was filled into the upper portion.

③ The pipeline of the equipment was purged with nitrogen.
④ The water content (460 ppm) and the oxygenated compound content (a carbonyl value of 10000 ppm) in the C9-C13 Fischer-Tropsch oil were detected, the water content in benzene was detected to be 450 ppm, and the C9-C13 Fischer-Tropsch oil and benzene were mixed in a benzene-to-olefin molar ratio of 20:1.

Steps of the Experiment:
① The equipment was rinsed by introducing benzene into the bed and was purged with nitrogen, with the rinsing repeated three times.
② The temperature of the reactor was adjusted to 200° C. Benzene was charged into the reactor such that a reaction pressure was 4 MPa.
③ After the pressure was constant, the raw material was switched to the benzene-olefin raw material, and the space velocity was set to be 0.5 $h^{-1}$.
④ Sampling began after the system was filled with liquid. The olefin conversion rate is calculated through a chromatographic analysis, and the final product is collected.

The reaction was performed for 400 h, and the olefin conversion rate for the reaction was 99%, the straight chain ratio was 97%, and the content of 2-position substituted product was 45%.

Example 2

Experimental instruments and chemicals: a high purity nitrogen, a quartz wool, a quartz sand or an inert ceramic balls, a fixed bend reactor, a piston pump, a C9-C13 Fischer-Tropsch oil, a benzene (99.9%), a YT-02 resin catalyst, and a gas chromatograph.

Preparation for the Experiment:
① The equipment was purged with an air pump; and the liquid transfer pump was calibrated.
② The catalyst was charged.

Quartz sand and quartz wool were added into the lower portion of the reactor, then the catalyst was mixed with inert ceramic balls in a certain proportion and loaded into the constant temperature zone, and quartz wool was filled into the upper portion.

③ The pipeline of the equipment was purged with nitrogen.
④ The water content (460 ppm) and the oxygenated compound content (a carbonyl value of 10000 ppm) in the C9-C13 Fischer-Tropsch oil were detected, the water content in benzene was detected to be 450 ppm, and the C9-C13 Fischer-Tropsch oil and benzene were mixed in a benzene-to-olefin molar ratio of 20:1.

Steps of the Experiment:
① The equipment was rinsed by introducing benzene into the bed and was purged with nitrogen, with the rinsing repeated three times.
② The temperature of the reactor was adjusted to 70° C. Benzene was charged into the reactor such that a reaction pressure was 4 MPa.
③ After the pressure was constant, the raw material was switched to the benzene-olefin raw material, and the space velocity was set to be 0.5 $h^{-1}$.

④ Sampling began after the system was filled with liquid. The olefin conversion rate is calculated through a chromatographic analysis, and the final product is collected.

The reaction was performed for 400 h, and the olefin conversion rate for the reaction was 60%, the straight chain ratio was 99%, and the content of 2-position substituted product was 52%.

Example 3

Experimental instruments and chemicals: a high purity nitrogen, a quartz wool, a quartz sand or an inert ceramic balls, a fixed bend reactor, a piston pump, a C9-C13 Fischer-Tropsch oil, a benzene (99.9%), a YT-02 resin catalyst, and a gas chromatograph.

Preparation for the experiment:
① The equipment was purged with an air pump; and the liquid transfer pump was calibrated.
② The catalyst was charged.

Quartz sand and quartz wool were added into the lower portion of the reactor, then the catalyst was mixed with quartz sand in a certain proportion and loaded into the constant temperature zone, and quartz wool was filled into the upper portion.
③ The pipeline of the equipment was purged with nitrogen.
④ The water content (460 ppm) and the oxygenated compound content (a carbonyl value of 10000 ppm) in the C9-C13 Fischer-Tropsch oil were detected, the water content in benzene was detected to be 450 ppm, and the C9-C13 Fischer-Tropsch oil and benzene were mixed in a benzene-to-olefin molar ratio of 20:1.

Steps of the Experiment:
① The equipment was rinsed by introducing benzene into the bed and was purged with nitrogen, with the rinsing repeated three times.
② The temperature of the reactor was adjusted to 200° C. Benzene was charged into the reactor such that a reaction pressure was 1 MPa.
③ After the pressure was constant, the raw material was switched to the benzene-olefin raw material, and the space velocity was set to be 0.5 h$^{-1}$.
④ Sampling began after the system was filled with liquid. The olefin conversion rate is calculated through a chromatographic analysis, and the final product is collected.

The reaction was performed for 400 h, and the olefin conversion rate for the reaction was 98%, the straight chain ratio was 97%, and the content of 2-position substituted product was 47%.

Example 4

Experimental instruments and chemicals: a high purity nitrogen, a quartz wool, a quartz sand or an inert ceramic balls, a fixed bend reactor, a piston pump, a C9-C13 Fischer-Tropsch oil, a benzene (99.9%), a YT-02 resin catalyst, and a gas chromatograph.

Preparation for the Experiment:
① The equipment was purged with an air pump; and the liquid transfer pump was calibrated.
② The catalyst was charged.

Quartz sand and quartz wool were added into the lower portion of the reactor, then the catalyst was mixed with quartz sand in a certain proportion and loaded into the constant temperature zone, and quartz wool was filled into the upper portion.
③ The pipeline of the equipment was purged with nitrogen.
④ The water content (460 ppm) and the oxygenated compound content (a carbonyl value of 10000 ppm) in the C9-C13 Fischer-Tropsch oil were detected, the water content in benzene was detected to be 450 ppm, and the C9-C13 Fischer-Tropsch oil and benzene were mixed in a benzene-to-olefin molar ratio of 20:1.

Steps of the Experiment:
① The equipment was rinsed by introducing benzene into the bed and was purged with nitrogen, with the rinsing repeated three times.
② The temperature of the reactor was adjusted to 200° C. Benzene was charged into the reactor such that a reaction pressure was 4 MPa.
③ After the pressure was constant, the raw material was switched to the benzene-olefin raw material, and the space velocity was set to be 5 h$^{-1}$.
④ Sampling began after the system was filled with liquid. The olefin conversion rate is calculated through a chromatographic analysis, and the final product is collected.

The reaction was performed for 400 h, and the olefin conversion rate for the reaction was 90%, the straight chain ratio was 98%, and the content of 2-position substituted product was 48%.

Example 5

Experimental instruments and chemicals: a high purity nitrogen, a quartz wool, a quartz sand, a fixed bend reactor, a piston pump, a C9-C13 Fischer-Tropsch oil, a benzene (99.9%), a YT-02 resin catalyst, and a gas chromatograph.

Preparation for the Experiment:
① The equipment was purged with an air pump; and the liquid transfer pump was calibrated.
② The catalyst was charged.

Quartz sand and quartz wool were added into the lower portion of the reactor, then the catalyst was mixed with quartz sand in a certain proportion and loaded into the constant temperature zone, and quartz wool was filled into the upper portion.
③ The pipeline of the equipment was purged with nitrogen.
④ The water content (460 ppm) and the oxygenated compound content (a carbonyl value of 10000 ppm) in the C9-C13 Fischer-Tropsch oil were detected, the water content in benzene was detected to be 450 ppm, and the C9-C13 Fischer-Tropsch oil and benzene were mixed in a benzene-to-olefin molar ratio of 1:1.

Steps of the Experiment:
① The equipment was rinsed by introducing benzene into the bed and was purged with nitrogen, with the rinsing repeated three times.
② The temperature of the reactor was adjusted to 200° C. Benzene was charged into the reactor such that a reaction pressure was 4 MPa.
③ After the pressure was constant, the raw material was switched to the benzene-olefin raw material, and the space velocity was set to be 0.5 h$^{-1}$.
④ Sampling began after the system was filled with liquid. The olefin conversion rate is calculated through a chromatographic analysis, and the final product is collected.

The reaction was performed for 400 h, and the olefin conversion rate for the reaction was 60%, the straight chain ratio was 99%, and the content of 2-position substituted product was 53%.

Comparative Example 1

Comparative Example 1 was performed in the same manner as Example 1, except that a Hβ zeolite was used as the catalyst instead of the YT-02 resin catalyst. The reaction only maintained 40 h (because the Hβ molecular sieve is afraid of water and oxygenated compounds, and thus the lifetime was reduced by around 90%), the olefin conversion rate for the reaction was 99%, the straight chain ratio was 97%, and the content of 2-position substituted product was 42%.

Comparative Example 2

Comparative Example 2 was performed in the same manner as Example 1, except that a HY zeolite was used as the catalyst instead of the YT-02 resin catalyst. The reaction only maintained 40 h (because the HY molecular sieve is afraid of water and oxygenated compounds, and thus the lifetime was reduced by around 90%), the olefin conversion rate for the reaction was 85% (the acidity of HY is less than that of Hβ, resulting in low conversion rate), the straight chain ratio was 97%, and the content of 2-position substituted product was 42%.

Comparative Example 3

Comparative Example 3 was performed in the same manner as Example 1, except that a strong acid cation exchange resin was used as the catalyst instead of the YT-02 resin catalyst. The reaction was performed for 400 h, the olefin conversion rate for the reaction was 99%, the straight chain ratio was 97%, and the content of 2-position substituted product was 15% (the resin has no pores and has no selectivity effect, so isomers substituted at each of the positions are almost the same as each other, such that the content of 2-position substituted product was less than that of the product with the molecular sieve catalyst).

The above description is only some preferred embodiments of the present invention. It should be noted that some modifications and variations can be made by one of ordinary skill in the art without departing from the principle of the present invention. These modifications and variations should also be regarded as falling within the protection scope of the present invention.

What is claimed is:

1. A method for preparing a coal-based linear alkylbenzene, the method comprising:
    preparing the coal-based linear alkylbenzene by an alkylation reaction using a coal-based Fischer-Tropsch synthetic oil and a benzene as reaction raw materials and using a molecular sieve loaded with a strong acid cation exchange resin as a catalyst,
    wherein the strong acid cation exchange resin has an acid strength ≥0.9 mmol/g [$H^+$], and
    wherein the coal-based Fischer-Tropsch synthetic oil comprises a linear olefin with a carbon number range of C9-C13.

2. The method according to claim 1, wherein a molar ratio of the benzene to the coal-based Fischer-Tropsch synthetic oil is in a range of (20-1):1.

3. The method according to claim 1, wherein the reaction raw materials are not subjected to a treatment of removing water or oxygenates therein.

4. The method according to claim 1, wherein the molecular sieve is one or more selected from the group consisting of a Hβ molecular sieve, a HY molecular sieve and a MCM molecular sieve.

5. The method according to claim 4, wherein the molecular sieve has a porous structure in which pores with a pore size of 1-10 nm account for 10-20%, and pores with a pore size of 100-200 nm accounts for 90-80%.

6. The method according to claim 1, wherein a mass ratio of the strong acid cation exchange resin to the molecular sieve is in a range of 1:9-4:6.

7. The method according to claim 1, wherein the alkylation reaction is carried out at a temperature in a range of 70-200° C. and a pressure in a range of 1-4 MPa and a space velocity in a range of 0.5-10 $h^{-1}$.

8. The method according to claim 1, wherein the coal-based Fischer-Tropsch synthetic oil has an oxygenated compound content in a range of 1-12000 ppm and a water content in a range of 1-550 ppm.

9. The method according to claim 1, wherein the benzene has a water content in a range of 1-550 ppm.

10. The method according to claim 1, wherein the strong acid cation exchange resin is loaded into pores and onto a surface of the molecular sieve.

* * * * *